US012629461B2

(12) United States Patent　　　(10) Patent No.:　US 12,629,461 B2

Stockerl et al.　　　　　　　　　　(45) Date of Patent:　May 19, 2026

(54) DEVICE FOR A MEDICAL TREATMENT APPARATUS FOR MEASURING THE FLOW OF FLUIDS IN A LUMEN TO BE INSERTED, AND ENSEMBLE HAVING A CORRESPONDING DEVICE AND A LUMEN

(71) Applicant: FRESENIUS MEDICAL CARE DEUTSCHLAND GMBH, Bad Homburg (DE)

(72) Inventors: Tobias Stockerl, Bad Homburg (DE); Martin Urban, Bad Homburg (DE); Arne Peters, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 18/718,807

(22) PCT Filed: Dec. 16, 2022

(86) PCT No.: PCT/EP2022/086293

§ 371 (c)(1),
(2) Date: Jun. 12, 2024

(87) PCT Pub. No.: WO2023/111237

PCT Pub. Date: Jun. 22, 2023

(65) Prior Publication Data

US 2025/0049997 A1　　Feb. 13, 2025

(30) Foreign Application Priority Data

Dec. 16, 2021　(DE) ..................... 10 2021 214 511.6

(51) Int. Cl.
　　*A61M 1/14*　　　(2006.01)
　　*A61M 1/36*　　　(2006.01)
　　*A61M 5/168*　　(2006.01)

(52) U.S. Cl.
　　CPC .......... *A61M 1/154* (2022.05); *A61M 1/3626* (2013.01); *A61M 5/16886* (2013.01);
　　　　　　(Continued)

(58) Field of Classification Search
　　CPC ................ A61M 1/154; A61M 1/1647; A61M 1/36225; A61M 1/3626; A61M 1/3663;
　　　　　　(Continued)

(56) References Cited

U.S. PATENT DOCUMENTS 4,545,259 A　　10/1985　Jensen et al.
5,463,906 A *　11/1995　Spani ........................ A61B 8/06
　　　　　　　　　　　　　　　73/861.27

(Continued)

FOREIGN PATENT DOCUMENTS

DE　　　10235033 B4　　7/2006
DE　　102011084171 A1　　5/2012

(Continued)

OTHER PUBLICATIONS

International Search Report and Written Opinion (with English translation of International Search Report) issued in corresponding International Patent Application No. PCT/EP2022/086293 mailed Mar. 22, 2023 (8 pages).

(Continued)

*Primary Examiner* — Kami A Bosworth
(74) *Attorney, Agent, or Firm* — Kilyk & Bowersox, P.L.L.C.

(57) ABSTRACT

The invention relates to a device (1) for a medical treatment apparatus, the device being configured for measuring a flow of liquids in a lumen (S) inserted in the device, the device having a receptacle (D) and a first ultrasonic transducer (US1), wherein the receptacle (D) of the device (1) has a first guide side (A) and a second guide side (P), so that the lumen(S) has approximately a trapezoidal course when the (Continued)

tube is inserted in the device, wherein the first ultrasonic transducer (US1) is arranged at a first trapezoid corner, and wherein the first ultrasonic transducer (US1) in operation is designed to perform a measurement in or against a direction of flow in the lumen(S). The invention furthermore relates to an ensemble comprising the device and the lumen.

20 Claims, 3 Drawing Sheets

(52) U.S. Cl.
CPC .............. *A61M 2205/0216* (2013.01); *A61M 2205/3334* (2013.01); *A61M 2205/3375* (2013.01)

(58) Field of Classification Search
CPC .............. A61M 3/022; A61M 5/16831; A61M 5/16886; A61M 5/172; A61M 60/523; A61M 60/816; A61M 2205/3334; A61M 2205/3375; A61M 2205/3379
See application file for complete search history.

(56) References Cited

U.S. PATENT DOCUMENTS

| | | | | |
|---|---|---|---|---|
| 7,673,527 | B2* | 3/2010 | Ehring | ................... G01F 1/662 |
| | | | | 73/861.28 |
| 2007/0062305 | A1 | 3/2007 | Muller | |
| 2009/0078047 | A1* | 3/2009 | Dam | ...................... G01N 29/02 |
| | | | | 73/606 |
| 2009/0188531 | A1* | 7/2009 | Boyle, Jr. | ............ B08B 9/0436 |
| | | | | 134/146 |
| 2013/0104667 | A1 | 5/2013 | Koyano | |
| 2019/0285450 | A1 | 9/2019 | Tsukigi et al. | |
| 2021/0325218 | A1 | 10/2021 | Dixon et al. | |
| 2023/0061369 | A1* | 3/2023 | Hennessy | .............. G01F 1/662 |

FOREIGN PATENT DOCUMENTS

| | | | |
|---|---|---|---|
| EP | | 3261708 B1 | 5/2022 |
| WO | | 2008053193 A1 | 5/2008 |

OTHER PUBLICATIONS

International Preliminary Report on Patentability issued in corresponding International Patent Application No. PCT/EP2022/086293 (English translation) dated Jun. 13, 2024 (7 pages).

* cited by examiner

1

DEVICE FOR A MEDICAL TREATMENT APPARATUS FOR MEASURING THE FLOW OF FLUIDS IN A LUMEN TO BE INSERTED, AND ENSEMBLE HAVING A CORRESPONDING DEVICE AND A LUMEN

This application is a National Stage Application of PCT/EP2022/086293, filed Dec. 16, 2022, which claims priority to German Patent Application No. 10 2021 214 511.6, filed Dec. 16, 2021.

The invention relates to a device for a medical treatment apparatus for measuring the flow of liquids in a lumen to be inserted and an ensemble comprising a corresponding device and a lumen.

BACKGROUND

In medical treatment apparatuses it is often required to measure the flow of a medium. The problem arises thereby that all elements of a medical treatment apparatus, which can could into contact with a patient to be treated, i.e. in particular liquid-conveying lumens, have to be capable of being sterilized.

Various means for measuring a flow are known from the prior art.

It is thus possible to measure the flow in a fixed arrangement by means of ultrasound. Such arrangements, however, are fixedly installed, so that, e.g. in the case of a medical treatment apparatus, the fixed arrangement has to be integrated into a fluid cycle. As a result, the arrangement has to be stabilized for the use on a patient. This is time-consuming, but also prone to errors. In the case of these fixed arrangements, this moreover often results in the disadvantage that a lateral inflow/outflow at a 90° angle to the measuring section is provided there. However, such angles often lead to strong turbulences, which can negatively impact the measurement.

To avoid this problem, solutions were developed in the past, in the case of which a disposable lumen has been observed by means of a clamp-like design. As a matter of principle, however, a signal is thereby coupled into the lumen or measured perpendicular to the flow (thus to the direction of flow). Arrangements, in the case of which two elements of the measuring arrangement (e.g. ultrasonic transducers) are offset along the lumen, i.e. one element lies upstream of the other element, are typical thereby. The measuring section formed in this way is typically only marginally longer because the offset is usually so slight that maximally an angle of 45° is formed between the direction of flow and the connecting line between the elements of the measuring arrangement, whereby the measuring section in comparison to perpendicular lengthens maximally to approx. 1.4-times the diameter of the lumen.

It has been shown that such measurements are in fact possible, but generally have a low resolution due to the measuring arrangement. The reason for this is that the time intervals to be determined are significantly smaller than in the case of a measurement in/against the direction of flow. The sensitivity of the measurement is furthermore also already low because the liquid volume, which is present in the measuring section at the same time, is almost minimal due to the almost perpendicular arrangement compared to arrangements with other angles or the measuring sections thereof, respectively. It is also apparent that the coupling is problematic because, on the one hand, the ultrasonic transducers have to have a good coupling, but, on the other hand, the contact pressure of the clamp-like design must not be too high, in order to be able to be handled at all by a human user in the clinical practice on the one hand, and in order to not compromise the measurement on the other hand. If such an arrangement is to be practicable for different lumen diameters, this is only possible to a very limited extent. In the case of the current designs, the handling of a disposable lumen is additionally associated with several operating steps, in order to provide the defined press-on properties of ultrasonic transducers to the disposable lumen before a measurement is possible due to the low resolution.

Object

Based on this, an object of the invention is to provide an improved arrangement, which offers a high measuring resolution for various lumen diameters with simple handling. An alternative or additional object of the invention is to avoid "sharp-edged" or unsteady geometries in the liquid lumen upstream of the measuring section, which lie so close to the measuring section that turbulences appear in the region of the measuring section.

BRIEF DESCRIPTION OF THE INVENTION

The object is solved by means of a device for a medical treatment apparatus for measuring the flow of liquids in a lumen to be inserted, having a receptacle and a first ultrasonic transducer, wherein the receptacle in the device has a first guide side and a second guide side, so that an inserted lumen has approximately a trapezoidal course in lateral projection, wherein the first ultrasonic transducer is arranged at a first trapezoid corner, and wherein the first ultrasonic transducer in operation is designed to perform a measurement in or against the direction of flow in the lumen, respectively.

With simple handling, this design provides a high measuring resolution for various lumen diameters.

In an embodiment of the invention, the device furthermore has a second ultrasonic transducer, wherein the second ultrasonic transducer is arranged at a second trapezoid corner, and wherein the second ultrasonic transducer in operation is designed to perform a measurement in or against the direction of flow in the lumen, respectively, in the opposite direction to the first ultrasonic transducer.

In an alternative of this embodiment, the device is designed in such a way that the second ultrasonic transducer performs measurements in conjunction with the first ultrasonic transducer, so that measurements are performed in both directions.

This design offers the advantage that measurements can be performed in the direction of flow as well as in the reverse direction of flow, so that a higher measuring accuracy can be provided.

According to an embodiment of the invention, the flow is measured by means of a time-of-flight method, in the case of which the time-of-flight of an ultrasonic signal is measured by an ultrasonic transducer along the measuring section, once with the direction of flow, and once against the direction of flow. A reflection at the end of the measuring section back in the initial direction can thus enable the measuring principle in the case of an arrangement comprising only one ultrasonic transducer, which first appears as transmitter and then as receiver, and both can alternately act as transmitter or receiver, respectively, in the case of an arrangement comprising two ultrasonic transducers.

According to an embodiment of the invention, the liquid to be measured is blood.

Special demands are made on the measurement of properties of blood. The device can thus be used in particular for blood treatment apparatuses, e.g. dialysis and apheresis apparatuses, and, in the context of extracorporeal blood circuits, e.g., for devices for the cardiac and/or lung support or replacement therapy.

According to an embodiment of the invention, the liquid to be measured is blood, another biological liquid, or dialysis substitute, or a medical liquid, such as a liquid medicine or a mixture of the above-mentioned liquids.

The device can thus be used in particular for blood treatment apparatuses, e.g. dialysis and apheresis apparatuses, and, in the context of extracorporeal blood circuits, e.g., for devices for the cardiac and/or lung support or replacement therapy.

According to an embodiment of the invention, the liquid to be measured is dialysate or another physiological replacement liquid, or a medical liquid, such as a liquid medicine or a mixture of the above-mentioned liquids.

The device can thus be used in particular for blood treatment apparatuses, such as dialysis apparatuses, dialysis dispensing arrangements, and apheresis apparatuses.

In a further embodiment of the invention, the liquid to be measured is liquid food, e.g. as special diet.

In a further embodiment of the invention, the device furthermore has a clamp, which can selectively interrupt an inserted lumen by means of cross-clamping.

In addition to measuring functions, it is made possible thereby to also provide switching functions, e.g. in a detected case of failure.

According to a further embodiment of the invention, the trapezoid is isosceles.

By means of an isosceles arrangement, the measuring technology can be set up in a mirror-inverted manner and thus with identical parts, whereby development as well as production costs decrease.

In yet a further embodiment of the invention, the device furthermore has an external evaluation means for controlling and evaluating ultrasonic transducer(s).

This means that an integrated structural unit can now be provided by means of the evaluation means.

According to yet a further embodiment of the invention, the device furthermore has at least one further sensor for measuring a further parameter of the liquid.

By means of the integration of further sensors, cost-efficient structural components with further measuring properties can be set up.

In a further embodiment of the invention, the device is furthermore configured to recognize micro-bubbles in the liquid, which are located in an inserted lumen, e.g. on the basis of fluctuation in measured flows.

Micro-bubbles can be signs of beginning problems as well as of errors, so that the recognition of micro-bubbles increases the safety. Advantageously, it plays a role thereby that the arrangement provides for a measurement at a larger liquid volume than in the case of the measuring arrangements, which are almost perpendicular (or also at an angle of 45°). A larger volume can thus also be measured simultaneously with regard to the presence of micro-bubbles. In an alternative of the embodiment, the presence of micro-bubbles is determined on the basis of fluctuations in the measuring signal, from which the flow is determined (e.g. time-of-flight difference of acoustic signals with and against the direction of flow), but not mandatorily directly from the measured variable alone, which is thus obtained, but an additional variable for evaluating the fluctuations in the measuring signal is used. This additional measured variable can be, e.g., amplitude information of the transmitted ultrasonic signal.

In a further embodiment, the device is configured to additionally determine a measured variable, which correlates with the density of the liquid to be measured.

In a further embodiment, the device is configured to additionally determine a measured variable, which correlates with the temperature of the liquid to be measured.

According to yet a further embodiment of the invention, the first guide side and the second guide side can be displaced relative to one another.

The bandwidth of lumen diameter can be increased particularly well thereby.

In yet a further embodiment of the invention, the first guide side and the second guide side exerts a defined and/or settable or force on an inserted lumen.

The ultrasonic transducer can thereby provide measurements with high accuracy in a favorable operating range.

According to yet a further embodiment of the invention, the one receptacle is designed for various diameters of insertable lumens.

In yet a further embodiment of the invention, the first guide side and the second guide side can be displaced jointly relative to a housing in a drawer-like manner.

A particularly good usability can be attained thereby.

According to a further design of the invention, an ensemble with a device for measuring according to the invention and a lumen is also provided.

This design provides for a high measuring resolution for various lumen diameters with simple usability.

According to an embodiment of the invention, the lumen is a disposable hose.

In an embodiment of the invention, the lumen is elastic.

Conventional hose systems as well as disposable articles can thus also be combined with the device according to the invention.

Further advantageous designs are subject matter of the respective dependent claims, of the figures, and of the description.

BRIEF DESCRIPTION OF THE FIGURES

The invention will be described in more detail below on the basis of a drawing and exemplary embodiments. The drawing is a schematic illustration and is not true to scale. The drawing does not limit the invention in any way.

DETAILED DESCRIPTION OF THE INVENTION

The invention will be described in more detail below with reference to the figures. It is important to note thereby that different aspects are described, which can in each case be used individually or in combination. This means that any aspect can be used with different embodiments of the invention, unless explicitly described as a pure alternative.

For the sake of simplicity, reference will furthermore generally always be made below only to one entity. Unless explicitly noted, the invention can, however, in each case also have several of the respective entities. In this respect, the use of the word "one" is to only be understood as reference to the fact that at least one entity is used in a simple embodiment.

Insofar as methods are described below, the individual steps of a method can be arranged and/or combined in any order, unless something different follows explicitly from the context. The methods—unless otherwise expressly identified—can furthermore be combined with one another.

Information with numerical values are generally not to be understood as exact values, but also include a tolerance of from +/−1% to +/−10%.

As far as standards, specifications, or the like are named in this application, reference is at least always made to the standards, specification, or the like, which are applicable on the filing date. This means that if a standard/specification, etc. is updated or replaced by a replacement, the invention is also applicable thereto.

Various embodiments are illustrated in the figures.

Figure 1:
FIG. 1 shows a schematic illustration of embodiments of the invention without inserted lumen.

In an embodiment of the invention, a device 1 for a medical treatment apparatus for measuring the flow of liquids in a lumen S to be inserted has a receptacle D and a first ultrasonic transducer US1. Reference will be made in an exemplary manner to FIG. 1 without lumen and to FIGS. 2, 3a, and 3b with lumen S. Ultrasonic transducers are available in various designs, but the invention in particular captures piezoelectric transducers.

The medical treatment apparatus is thereby in particular a blood treatment apparatus, such as, e.g., an apparatus for the oxygenation of blood, an apparatus for removing soluble component parts from blood, such as, e.g., a blood dialysis apparatus. Dialysis is to be understood broadly thereby and can mean in particular hemodialysis, hemodiafiltration, peritoneal dialysis, hemoultrafiltration, apheresis, etc., that is, in particular any type of kidney or liver replacement therapy.

The receptacle D in the device 1 has a first guide side A and a second guide side P, so that an inserted lumen S has approximately a trapezoidal course in lateral projection, wherein the first ultrasonic transducer US1 is arranged at a first trapezoid corner, and wherein the first ultrasonic transducer US1 in operation is designed to perform a measurement in or against the direction of flow in the lumen S, respectively.

It is important to note thereby that the exact direction of the measurement by means of the first ultrasonic transducer US1 is left up to the design by the person of skill in the art, so that the (triangularly illustrated) arrangement sketched in the figures is only an example. This means that the ultrasonic transducer can in particular also be arranged so that the measuring direction is not arranged in the direction of one of the horizontally illustrated arrows, it would likewise be conceivable that measurement could be performed in the direction of the dashed line in FIG. 2.

It is furthermore important to note that trapezoidal is only used to describe spatial orientations in order to illustrate a guidance of the lumen, whereby section meet one another, which draw an angle of unequal to 90°. This is illustrated in the figures by the angle α.

It is also important to note that the measuring principle can be designed differently. In addition to the principle of the time-of-flight measurement, it is also possible to use Doppler methods (frequency shifts by (back) scattering on the moving object) to determine flow speeds of the (medical) liquid to be examined in the lumen S, but without being limited thereto.

This design provides for a high measuring resolution for various lumen diameters with simple usability.

In an embodiment of the invention, the device 1 furthermore has a second ultrasonic transducer US2, wherein the second ultrasonic transducer US2 is arranged at a second trapezoid corner, and wherein the second ultrasonic transducer US2 during operation is designed to perform a measurement in or against the direction of flow in the lumen S, respectively, in the opposite direction to the first ultrasonic transducer US1.

This design offers the advantage that measurement can be performed in as well as against the direction of flow, so that a higher measuring accuracy can be provided. Such a measurement can thereby take place either independently, i.e. in reflection of a respective ultrasonic transducer into the lumen, and from there back to the same ultrasonic transducer, or dependently, that is, in transmission from an ultrasonic transducer through the lumen to the other ultrasonic transducer. This can be dependent on the distance of the ultrasonic transducers from one another, on the type of the lumen, the measuring frequency, or the liquid to be measured or its component parts, respectively, etc. A changing operation of ultrasonic transducers in transmission or reflection, respectively, can obviously also take place by means of a targeted control.

Due to the fact that measurements from different directions now become possible, measuring results can be included both in a common calculation and can be used for averaging.

According to an embodiment of the invention, the liquid to be measured is blood.

Special demands are made on the measurement of properties of blood. The device can thus be used in particular for medical blood treatment apparatuses, such as, e.g., an apparatus for the oxygenation of blood, e.g. for devices for the cardiac and/or lung support or replacement therapy, an apparatus for removing (soluble) component parts from blood, such as, e.g., a blood dialysis apparatus. Dialysis is to be understood broadly thereby and can mean, in particular, hemodialysis, hemodiafiltration, peritoneal dialysis, hemoultrafiltration, apheresis, etc., that is, in particular any type of kidney or liver replacement therapy.

According to an embodiment of the invention, the liquid to be measured is blood, another biological liquid, or dialysis substitute, or a medical liquid, such as a liquid medicine or a mixture of the above-mentioned liquids.

The device can thus be used in particular for blood treatment apparatuses, e.g. dialysis and apheresis apparatuses, and, in the context of extracorporeal blood circuits, e.g., for devices for the cardiac and/or lung support or replacement therapy.

According to an embodiment of the invention, the liquid to be measured is dialysate or another physiological replacement liquid, or a medical liquid, such as a liquid medicine or a mixture of the above-mentioned liquids.

The device can thus be used in particular for blood treatment apparatuses, such as dialysis apparatuses, dialysis dispensing arrangements, and apheresis apparatuses.

In a further embodiment of the invention, the liquid to be measured is liquid food, e.g. as special diet.

In a further embodiment of the invention, the device furthermore has a clamp, which can selectively interrupt an inserted lumen S by means of cross-clamping.

In addition to measuring functions, it is made possible thereby to also provide switching functions, e.g. in a detected case of failure. For example, air in the lumen S can be a reason that, e.g., a treatment by means of a blood treatment device is stopped.

By providing a clamp in the device, the process of the insertion of a lumen can furthermore be simplified, because such a clamp has to often be arranged in the flow path in the further course of the lumen S, e.g. in the case of a blood treatment apparatus. This means that operating steps can be avoided by means of the integrated arrangement, whereby the setup times decrease.

A suitable clamp can be integrated into the device 1. For example, a clamp-illustrated as triangles in FIG. 2—can be integrated at a suitable location. The clamp preferably does not exert any pressure on the ultrasonic transducers US1, US2.

According to a further embodiment of the invention, the trapezoid is isosceles, as shown by the angle α in the figures.

By means of an isosceles arrangement, the measuring technology can be set up in a mirror-inverted manner and thus with identical parts, whereby development as well as production costs decrease.

In yet a further embodiment of the invention, the device furthermore has an (external) evaluation means M for controlling and evaluating ultrasonic transducer(s). As sketched in FIG. 1, the evaluation means M can control, for example, the ultrasonic transducers US1, US2 and can also receive data/measured values from the ultrasonic transducers US1, US2.

This means that an (integrated) structural unit can now be provided by means of the evaluation means.

According to yet a further embodiment of the invention, the device furthermore has at least one further sensor S1, S2, S3 for measuring a further parameter of the liquid. The sensors S1, S2 can thereby be arranged individually or also as group S3. For example, the sensor S1 can be a temperature sensor, while the sensor S2 is a reflective optical sensor or the sensor S3 could be a transmissive optical sensor, respectively. E.g., air bubbles, component parts and the concentrations thereof, density, temperature, etc., can be determined by means of such sensors.

By means of the integration of further sensors, cost-efficient structural components with further measuring properties can be set up.

In a further embodiment of the invention, the device is furthermore configured to recognize micro-bubbles in the liquid, which are located in an inserted lumen S, e.g. on the basis of fluctuation in measured flows.

Micro-bubbles can be signs of beginning problems as well as of errors, so that the recognition of micro-bubbles increases the safety. Advantageously, it plays a role thereby that the arrangement provides for a measurement at a larger liquid volume than in the case of the measuring arrangements, which are almost perpendicular (or also at an angle of) 45°. A larger volume can thus also be measured simultaneously with regard to the presence of micro-bubbles. In an alternative of the embodiment, the presence of micro-bubbles is determined on the basis of fluctuations in the measuring signal, from which the flow is determined (e.g. time-of-flight difference of acoustic signals with and against the direction of flow), but not mandatorily directly from the measured variable alone, which is thus obtained, but an additional variable for evaluating the fluctuations in the measuring signal is used. This additional measured variable can be, e.g., amplitude information of the transmitted ultrasonic signal.

Figure 2:
FIG. 2 shows a schematic illustration of embodiments of the invention with inserted lumen.

According to yet a further embodiment of the invention, the first guide side A and the second guide side P can be displaced relative to one another, as can be seen from FIGS. 1 and 2.

The bandwidth of lumen diameters can be increased particularly well thereby. The contact pressure can likewise be capable of being set in a suitable manner, so that the ultrasonic transducers US1, US2 can use a favorable operating range.

In yet a further embodiment of the invention, the first guide side A and the second guide side P exert a defined force, in particular a settable force, on an inserted lumen S.

It is further important to note that a catch mechanism can also be provided, so that, e.g., a certain contact pressure can be maintained.

The ultrasonic transducer can thereby provide measurements with high accuracy in a favorable operating range.

According to yet a further embodiment of the invention, a receptacle is designed for various diameters of insertable lumens S.

It is important to note that the provision of a device for disposable lumens offers significant advantages, because only few parts have to now be sterilized easily.

Figures 3A, 3B:
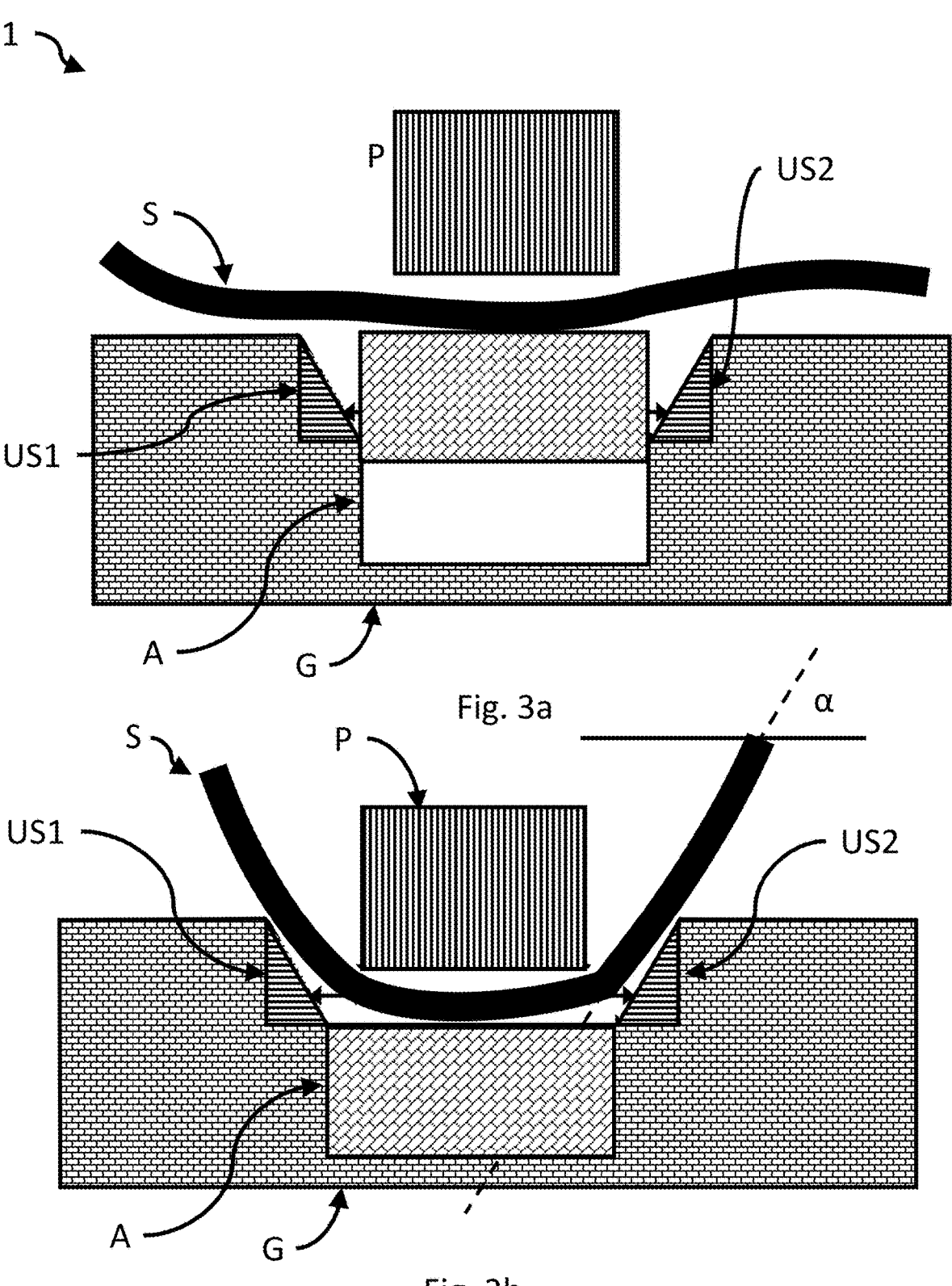
FIGS. 3a and 3b show a schematic illustration of further aspects of embodiments of the invention.

In yet a further embodiment of the invention—as illustrated in FIGS. 3a and 3b—the first guide side A and the second guide side P can be displaced jointly in a drawer-like manner relative to a housing G. Due to this drawer-shaped design, the desired forced path for the lumen S is provided during the insertion of the drawer together with the housing G, so that all of the above-mentioned advantages can also be realized in this embodiment. Even though the forced path is described as trapezoidal above, this does not rule out that a W-shape or a V-shape, or an S-shape is also provided in sections.

Without limiting the generality, the receptacle D can also be constructed of several (injection molded) components. For example, a trough-like lower part can be provided, into which a top part is inserted (linearly), into which the lumen S can be inserted easily (e.g. laterally/normally to the insertion direction). The ultrasonic transducers US1, US2 can thereby be arranged at the top part or at the lower part. The only important factor is that the ultrasonic transducers US1, US2 abut against the lumen S for a coupling in the joined state.

Without limiting the generality, such an insertion movement (or also a contact pressure) can be provided manually or in a supported manner or in an automated manner (by means of spring forces, electric drives, compressed air, etc.).

According to a further design of the invention, an ensemble with a device for measuring according to the invention and a lumen is also provided.

This design provides for a high measuring resolution for various lumen diameters with simple usability.

According to an embodiment of the invention, the lumen S is a disposable hose, in particular a disposable hose for a medical liquid, such as, e.g., blood, a dialysate inlet, a permeate inlet, a dialysate outlet, etc.

In an embodiment of the invention, the lumen S is elastic. The lumen S can in particular be made of a suitable optically transparent fabric.

Conventional hose systems as well as disposable articles can thus also be combined with the device according to the invention.

It is important to note that the coupling is an important aspect during the measurement with ultrasound, i.e. by means of ultrasonic transducers US1, US2. The coupling is dependent on the impedance between lumen S and ultrasonic transducers US1, US2. The impedance is largely dependent on the presence of air. This means that if the lumen S is pressed against the ultrasonic transducer(s) US1, US2 with sufficient force, the presence of air between the lumen S and the ultrasonic transducers US1, US2 is low and a good coupling exists.

In current clamping arrangements, which provided a coupling or measurement perpendicular to the direction of flow or perpendicular, but slightly offset (up to 45°) arrangement, the contact pressure effected a deformation of the lumen, so that even though the latter abutted better against the ultrasonic transducers, the contact pressure (caused by the elasticity of the lumen) was simultaneously negative for the measurement. Moreover, the contact pressure in the case of different lumens was highly dependent on the size of the lumen, the material thickness of the lumen, as well as the material of the lumen. This means that the variance of the lumens made it almost impossible until now to provide a similarly good measuring result for all differently usable lumens. In the past, this had the result that only a small sub-quantity was approved for the use with a certain measuring device. In addition, a measuring arrangement had to often be calibrated to the respective individual hose type, so that a difficulty also already existed for that reason alone.

In contrast to the prior art, an orientation of the measuring section perpendicular to the guide/fixation is now provided, so that the problematic of the coupling as well as of the measuring range as well as of the variability of the lumens can be solved on the one hand. On the contrary, it is also possible as part of the device according to the invention to vary a contact pressure during an on-going treatment/measurement. Depending on the measurement, e.g., a measuring signal of the ultrasonic transducer or of a sensor S1 . . . . S3 can be returned, in order to track, e.g., the contact pressure in a variable manner, so that a desired signal stroke can be realized.

Due to the fact that a measurement in/against the direction of flow is now made possible in the invention, the measuring intervals for time-of-flight differences can be increased. An improved signal-to-noise ratio can thus be attained. Due to the longer design of the measuring section, the demands on the required time resolution additionally decrease during the measurement of the time-of-flight difference, which provides for more favorable realizations.

In contrast to the current approaches, it is additionally possible to not only recognize micro-bubbles qualitatively, but also to quantify them. Due to the longer measuring section and effects, which during the inlet and outlet of the air, as well as during the longer dwell time in the measuring section, the air can be detected and quantified better. A simpler determination of air quantities results due to an integral volume, which, viewed in the measuring section—in contrast to one used in the current prior art only 2-dimensional cross section.

The ratio of hose wall to measuring section is optimized during the adaptation. This has the result that the measurements are more independent of tolerances of the hose walls. A larger portion of the measuring section is in particular not deformed, because no coupling of the sensor system is required at the largest.

The invention claimed is:

1. A device for a medical treatment apparatus, the device configured for measuring a flow of liquids in a lumen of a tube when the tube is inserted in the device, the device comprising a first guide side, a second guide side, and a first ultrasonic transducer, wherein a receptacle is defined in the device by the first guide side and the second guide side, wherein the receptacle defines a trapezoidal shape configured to receive the tube therein such that the lumen of the tube has approximately a trapezoidal course when the tube is inserted in the receptacle of the device, wherein the first ultrasonic transducer is arranged within the receptacle and at a first trapezoid corner, and wherein the first ultrasonic transducer in operation is designed to perform a measurement in or against a direction of flow in the lumen.

2. The device according to claim 1, wherein the device furthermore has a second ultrasonic transducer, wherein the second ultrasonic transducer is arranged at a second trapezoid corner of the receptacle, and wherein the second ultrasonic transducer in operation is designed to perform a measurement in or against the direction of flow in the lumen in an opposite direction to the first ultrasonic transducer.

3. The device according to claim 1, wherein the liquid is blood, a biological liquid other than blood, a physiological replacement liquid, or a medical liquid.

4. The device according to claim 1, wherein the device furthermore has a clamp, which is capable of being able to selectively interrupt the lumen by means of cross-clamping when the tube is inserted in the device.

5. The device according to claim 1, wherein the trapezoid is isosceles.

6. The device according to claim 1, wherein the device furthermore has an external evaluation means for controlling and evaluating at least the first ultrasonic transducer.

7. The device according to claim 1, wherein the device furthermore has at least one further sensor for measuring a further parameter of the liquid.

8. The device according to claim 1, wherein the device is furthermore configured to recognize micro-bubbles in the liquid in the lumen when the tube is inserted in the device.

9. The device according to claim 8, wherein the device is furthermore configured to recognize the micro-bubbles in the liquid on the basis of fluctuation in the flow in the lumen.

10. The device according to claim 1, wherein the first guide side and the second guide side are capable of being displaced relative to one another.

11. The device according to claim 10, wherein the first guide side and the second guide side exert a defined force on the tube when the tube is inserted in the device, wherein the defined force effects a deformation of the lumen.

12. The device according to claim 10, wherein the first guide side and the second guide side exert a settable force on the tube when the tube is inserted in the device, wherein the settable force effects a deformation of the lumen.

13. The device according to claim 1, wherein the receptacle is designed for various diameters of insertable lumens.

14. The device according to claim 1, wherein the first guide side and the second guide side are capable of being displaced jointly relative to a housing in a drawer-like manner.

15. The device according to claim 1, wherein the liquid is a dialysate, dialysis substitution fluid, a liquid medicine, a mixture of the above-mentioned liquids, or liquid food.

16. The device according to claim 1, wherein the tube is elastic.

17. An ensemble comprising a device for a medical treatment apparatus and a tube, the device configured for measuring a flow of liquids in a lumen of the tube when the tube is inserted in the device, the device comprising a first guide side, a second guide side, and a first ultrasonic transducer, wherein a receptacle is defined in the device in between the first guide side and the second guide side, wherein the receptacle defines a trapezoidal shape configured to receive the tube therein such that the lumen of the tube has approximately a trapezoidal course when the tube is inserted in the receptacle of the device, wherein the first ultrasonic transducer is arranged at a first trapezoid corner of the receptacle, and wherein the first ultrasonic transducer in operation is designed to perform a measurement in or against a direction of flow in the lumen.

18. The ensemble according to claim 17, wherein the tube is a disposable hose.

19. The ensemble according to claim 17, wherein the tube is elastic.

20. A device for a medical treatment apparatus, the device configured for measuring a flow of liquids in a lumen of a tube when the tube is inserted in the device, the device comprising a first guide side, a second guide side, and a first ultrasonic transducer, wherein a receptacle is defined in the device in between the first guide side and the second guide side, wherein the receptacle defines a trapezoidal shape configured to receive the tube therein such that the lumen of the tube has approximately a trapezoidal course when the tube is inserted in the receptacle of the device, wherein the first ultrasonic transducer is arranged at a first trapezoid corner of the receptacle, wherein the first ultrasonic transducer in operation is designed to perform a measurement in or against a direction of flow in the lumen, wherein the first guide side and the second guide side are capable of being displaced relative to one another, and the first guide side and the second guide side are configured to exert a defined and/or settable force that effects a deformation of the lumen when the tube is inserted in the receptacle of the device.

\* \* \* \* \*